United States Patent [19]

Yoo

[11] Patent Number: 4,484,573
[45] Date of Patent: Nov. 27, 1984

[54] ALARM DEVICE FOR USE IN A BABY'S DIAPER

[75] Inventor: Kil-Soo Yoo, Inchon, Rep. of Korea

[73] Assignee: Naewae Electric Co., Ltd., Seoul, Rep. of Korea

[21] Appl. No.: 400,816

[22] Filed: Jul. 22, 1982

[51] Int. Cl.³ .............................................. A61B 19/00
[52] U.S. Cl. .............................................. 128/138 A
[58] Field of Search .................. 128/138 A; 340/604; 604/361

[56] References Cited

U.S. PATENT DOCUMENTS

| 2,874,695 | 2/1959 | Vaniman | 128/138 A |
| 3,441,019 | 4/1969 | Snyder | 128/138 A |
| 3,460,123 | 8/1969 | Bass | 128/138 A |
| 3,678,928 | 7/1972 | Mozes | 128/138 A |
| 4,106,001 | 8/1978 | Mahoney | 128/138 A X |

Primary Examiner—John D. Yasko
Attorney, Agent, or Firm—Flynn, Thiel, Boutell & Tanis

[57] ABSTRACT

An alarm device for detecting moisture in a baby's diaper includes a housing having a moisture detector and a buzzer on the outer surface thereof. A space is provided within the housing, and a circuit board disposed in such space has an electronic circuit and a battery thereon. The electronic circuit is electrically connected to the moisture detector, the buzzer and the battery, and actuates the buzzer when the moisture detector indicates moisture is present in the diaper. Tie-rings are preferably provided on the housing for securing the alarm device to the baby's diaper.

9 Claims, 5 Drawing Figures

ALARM DEVICE FOR USE IN A BABY'S DIAPER

FIELD OF THE INVENTION

The present invention relates to an alarm for use in a baby's diaper and, more particularly, to a diaper alarm in which a buzzer sounds after a fecal excretion is detected.

BACKGROUND OF THE INVENTION

Up to this time, a baby's excrement has been detected only by opening the baby's diaper, so that there were disadvantages such as conditions unsanitary for the baby and the potential for skin diseases.

Accordingly, one object of the present invention is to provide a device adapted to produce a prompt and reliable indication of the presence of excrement in a baby's diaper.

SUMMARY OF THE INVENTION

According to the present invention, the presence of the baby's excrement is indicated by the sounding of a buzzer provided in the diaper in response to detection of moisture from the excrement which is absorbed by the diaper. Thus, the baby can be effectively protected from unsanitary conditions and skin diseases.

The alarm device of the present invention is preferably sufficiently small as to be placed at the outer surface of the diaper or at the inner surface of the baby's panties, if desired.

BRIEF DESCRIPTION OF THE DRAWINGS

The present invention will be described according to the drawings, in which.

DETAILED DESCRIPTION

Figure 1:
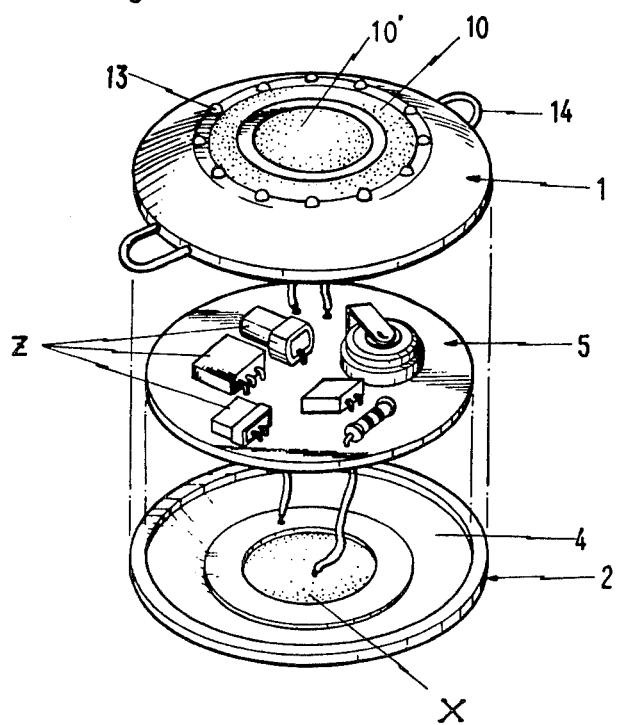
FIG. 1 is an exploded perspective view of an alarm device for use in baby's diaper and embodying the present invention.
Figure 2:
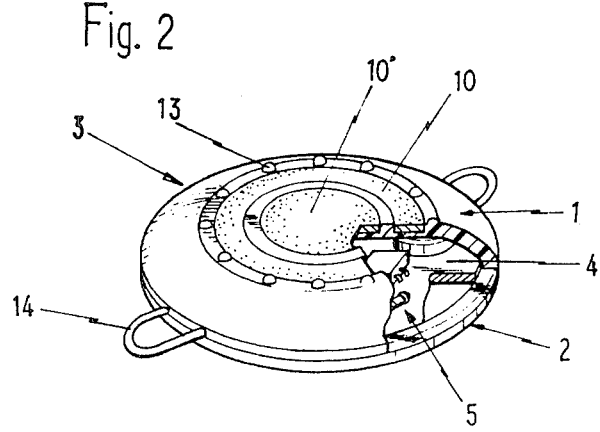
FIG. 2 is a fragmentary perspective view of the alarm device of FIG. 1.
Figure 3:
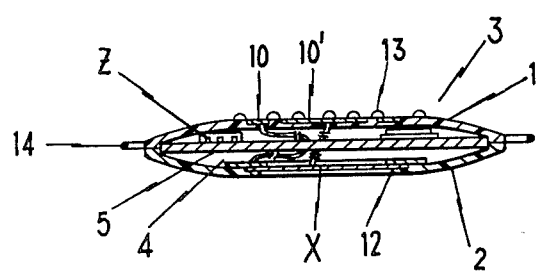
FIG. 3 is a sectional view of the alarm device in FIG. 1.
Figure 4:
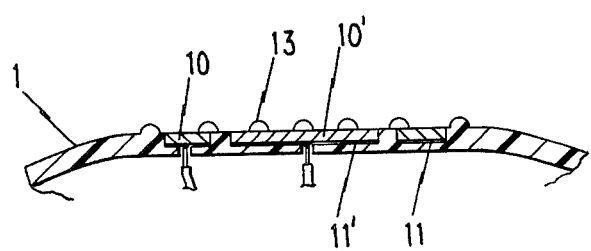
FIG. 4 is an enlarged view of part of FIG. 3.

As shown in FIGS. 1, 2, 3 and 4, an alarm device 3 has a housing which includes a case 1 and cover 2 having a circular, square, polygon or other shape perimeter, here, circular. A space 4 is formed between the case 1 and cover 2, and an insulated circuit board 5 having an electronic circuit Z thereon is disposed in the space 4. A detecting part 10 of ring shape and a detecting part 10' of circular shape are concentrically set into recesses 11 and 11', respectively, and the ring shaped detecting part 10 and circular detecting part 10' are electrically connected with the electronic circuit Z, the recesses 11 and 11' being centrally formed in the case 1.

A buzzer X is secured to the inside of the cover 2 by securing the edges of the buzzer X to the cover inner surface around a round hole 12 formed in the center of the cover 2.

A number of projections 13 are formed on the case 1 along the outer edge of the detecting part 10 in order to prevent the case 1 from slipping. Two tie-rings 14 are furnished on opposite sides of the case 1.

Figure 5:
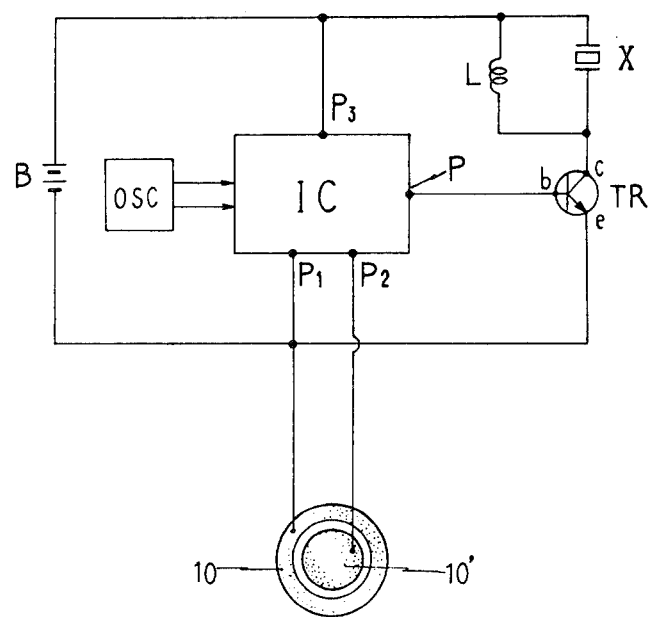
FIG. 5 is a schematic diagram of a circuit which is part of the device of FIG. 1.

As shown in FIG. 5, the circuit used in the alarm device 3 is designed so that electricity is supplied from the battery B to integrated circuit IC through the electric wires $P_1$ and $P_3$, integrated circuit IC is connected by wires $P_1$ and $P_2$ to the detecting parts 10 and 10', and oscillator OSC is connected directly to the integrated circuit IC, and the terminal P of the integrated circuit IC is connected with the base b of a transistor TR. The collector c of transistor TR is connected to one end of the buzzer X, the other end of the buzzer X is connected to the battery B, a coil L is connected in parallel with the buzzer X, and the emitter e of the transistor TR is directly connected to the negative power supply terminal of the battery B.

The detecting parts 10 and 10' are preferably made of a conductive metal, moisture which comes into contact therewith providing a path for the flow of electricity between the detecting parts 10 and 10'.

In using the present invention, the alarm device 3 is positioned appropriately in a baby's diaper or panties so as to allow the detecting parts 10 and 10' to contact the diaper. In placing the alarm device 3 inside of panties, the tie-rings 14 are used for securing it to the panties with some appropriate fastener.

When the baby relieves itself, moisture is absorbed by the diaper and the detecting parts 10 and 10' of the alarm device 3 detect the moisture and cause integrated circuit IC to send a signal to the base b of the transistor TR which is amplified by the transistor TR and causes the buzzer X to oscillate and produce an audible alarm indicating excrement is present. At this time, the coil L resonates with the buzzer X to make the alarm sound louder by increasing the voltage of the oscillations.

The oscillator OSC supplies a frequency required by the integrated circuit IC.

The alarm device 3 of the present invention produces the alarm by means of the electronic circuit Z which is placed in the space 4 formed between the case 1 and cover 2 and made with small dimensions, and the detecting parts 10 and 10' are fixed in the recesses 11 and 11', respectively, to make the overall dimensions of the alarm device smaller.

As hereinbefore mentioned, the detecting parts 10 and 10' contact the diaper during use so that the parts 10 and 10' can detect any excrement immediately, and the buzzer X is secured inside the cover 2 and over a round hole 12 provided in the middle part of the cover 2. Thus, all the essential parts are put into the case 1 and cover 2, which are preferably made of flat plastic and of small size so that the alarm device is very handy to use and a baby can be protected from unsanitary conditions and skin diseases.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An alarm device for use in a baby's diaper, comprising a circuit board having an electronic circuit thereon and provided in the space formed between a case and a cover, a ring-shaped detecting part and a round-shaped detecting part being fixed into recesses formed in the middle part of the outer surface of said case, said ring-shaped detecting part being concentric with and spaced apart from said round-shaped detecting part, and a buzzer being secured inside of said cover and over a round hole formed in the middle of said cover for producing an alarm when said detecting parts contact moisture in the baby's diaper such that electricity flows between said detecting parts.

2. An alarm device for use in a baby's diaper, comprising a circuit board having an integrated circuit thereon and provided in the space formed between a case and a cover, a ring-shaped detecting part and a round-shaped detecting part fixed into recesses formed in the middle part of the outer surface of said case, and a buzzer secured inside of said cover and over a round hole formed in the middle of said cover for producing an alarm when said detecting parts contact moisture in the baby's diaper, wherein electric wires from said integrated circuit, to which electricity is supplied from a battery, are connected to said detecting parts, an oscillator is connected directly with said integrated circuit, a terminal of said integrated circuit is connected with the base of a transistor, the collector of said transistor is connected to one end of said buzzer, the other end of said buzzer is connected to said battery, a coil is connected in parallel with said buzzer, and the emitter of said transistor is connected to said battery.

3. The alarm device of claim 1, including a plurality of projections provided on said case in the region of said detecting parts, and including at least one tie-ring provided on said case for securing said alarm device to the diaper.

4. An alarm device as claimed in claim 3, wherein said case and said cover are circular and fit together to form a disk-shaped unit, said projections are provided in a circular formation surrounding said detecting parts, and said alarm device has a pair of said tie-rings which extend radially outwardly in opposite directions from said disk-shaped unit.

5. An alarm device as claimed in claim 1, wherein said ring-shaped detecting part and said round-shaped detecting part are fixed into said recesses, said recesses being formed in the outer surface of said case so as to produce an alarm sound when said detecting parts contact a wet diaper, and stop producing the alarm sound when said detecting parts are released from contact with the wet diaper.

6. An alarm device for use in a baby's diaper, comprising a compact and substantially closed disk-shaped housing defining therein an interior space, said housing being defined by a disk-shaped cover and a disk-shaped case which are disposed in opposed relation to define said space therebetween said case and cover having peripheral edge portions which are abuttingly and fixedly joined together, a circuit board positioned within said space and fixedly positioned relative to said housing, said circuit board having an electronic circuit thereon, first and second electrically conductive detecting parts fixed to said housing and positioned adjacent the exterior surface thereof for exposure to moisture externally of the housing, said detecting parts being spaced apart in electrically nonconductive relationship to one another, first and second conductive elements positioned within said housing and electrically connecting said circuit to said first and second detecting parts respectively, and audible sound-generating means secured inside of said housing and connected to said circuit for producing an alarm when said detecting parts contact moisture in the baby's diaper.

7. An alarm device as claimed in claim 6, wherein said first detecting part is ring-shaped and surrounds said second detecting part.

8. An alarm device as claimed in claim 6, wherein said sound generating means comprises a buzzer which extends over a hole formed in said housing.

9. An alarm device as claimed in claim 6, wherein said detecting parts are substantially flush with the outer surface of said case.

* * * * *